United States Patent
Kamei et al.

(10) Patent No.: US 8,734,771 B2
(45) Date of Patent: May 27, 2014

(54) POWDER TREATED WITH A POWER TREATING AGENT COMPRISING AN ORGANOPOLYSILOXANE AND COSMETIC COMPRISING THE POWDER

(75) Inventors: Masanao Kamei, Annaka (JP); Kiyomi Tachibana, Tokyo (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 1223 days.

(21) Appl. No.: 11/712,420

(22) Filed: Mar. 1, 2007

(65) Prior Publication Data

US 2007/0207176 A1 Sep. 6, 2007

(30) Foreign Application Priority Data

Mar. 3, 2006 (JP) ................................. 2006-058674

(51) Int. Cl.
| | | |
|---|---|---|
| *A61Q 1/12* | (2006.01) | |
| *A61Q 1/06* | (2006.01) | |
| *A61Q 1/10* | (2006.01) | |
| *A61Q 5/00* | (2006.01) | |
| *A61Q 15/00* | (2006.01) | |
| *A61Q 19/00* | (2006.01) | |

(52) U.S. Cl.
USPC ............. 424/78.07; 424/47; 424/59; 424/64; 424/65; 424/69; 424/70.7; 424/70.12; 424/401

(58) Field of Classification Search
None
See application file for complete search history.

(56) References Cited

U.S. PATENT DOCUMENTS

| | | | | |
|---|---|---|---|---|
| 5,219,560 A | * | 6/1993 | Suzuki et al. | .................. 424/63 |
| 5,538,793 A | | 7/1996 | Inokuchi et al. | |
| 5,578,381 A | * | 11/1996 | Hamada et al. | ............... 428/447 |
| 5,683,527 A | * | 11/1997 | Angell et al. | .................. 156/78 |
| 6,660,281 B1 | | 12/2003 | Nakanishi et al. | |
| 6,717,003 B2 | * | 4/2004 | Nakanishi et al. | ............ 556/437 |
| 2002/0037963 A1 | | 3/2002 | Hara et al. | |
| 2004/0234477 A1 | * | 11/2004 | Sakuta | ....................... 424/70.12 |

FOREIGN PATENT DOCUMENTS

| | | |
|---|---|---|
| EP | 0661334 A1 | 7/1995 |
| EP | 1010714 A1 | 6/2000 |
| EP | 1174468 A1 | 1/2002 |
| EP | 1416016 A1 | 5/2004 |
| JP | 05-004129B2 A | 1/1993 |
| JP | 7-196815 | 8/1995 |
| JP | 8-73809 | 3/1996 |
| JP | 10-195217 A | 7/1998 |
| JP | 2000-191787 A | 7/2000 |
| JP | 2000-319542 A | 11/2000 |
| JP | 2001-72891 A | 3/2001 |
| JP | 2002-38016 A | 2/2002 |
| JP | 2002-363445 A | 12/2002 |
| JP | 2003-95655 A | 4/2003 |
| JP | 2003-95839 A | 4/2003 |
| WO | WO 03029375 A1 | 4/2003 |

* cited by examiner

*Primary Examiner* — Jyothsna Venkat

(74) *Attorney, Agent, or Firm* — Birch, Stewart, Kolasch & Birch, LLP

(57) ABSTRACT

Powder treated with a powder treating agent comprising organohydrogenpolysiloxane, characterized in that the organohydrogenpolysiloxane has a weight average molecular weight of from 300 to 100,000, at least one SiH bond per molecule, and at least one selected from $(R^2{}_3SiO_{1/2})$ unit and $(SiO_2)$ unit, wherein $R^1$ is selected from the group consisting of a hydrogen atom, and alkyl, fluorinated alkyl, aryl and aralkyl groups each having 1 to 30 carbon atoms.

18 Claims, No Drawings

POWDER TREATED WITH A POWER TREATING AGENT COMPRISING AN ORGANOPOLYSILOXANE AND COSMETIC COMPRISING THE POWDER

CROSS REFERENCE TO RELATED APPLICATION

This application claimed the benefit of the Japanese Patent Application No. 2006-058674 filed on Mar. 3, 2006, the contents of which are incorporated by reference.

FIELD OF THE INVENTION

The present invention relates to powder treated with a powder treating agent comprising an organohydrogenpolysiloxane. The organohydrogenpolysiloxane has a specific branched structure to be highly reactive with powder. The present invention also relates to a cosmetic comprising the powder. The cosmetic is stable with time and good to the touch. It forms durable makeup.

PRIOR ART

Powder such as those of titanium oxide and zinc oxide is used for various cosmetics such as sunscreens and powder or liquid foundations. It is known that these powders are surface treated with an organopolysiloxane to deactivate polar groups on surface thereof in order to prevent adsorption of water and to improve their dispersibility in oily media.

For example, Japanese Patent Application Laid-Open No. 2003-95655, and No. 2003-95839 describe methylhydrogenpolysiloxane and dimethylmethylhydrogenpolysiloxane represented by the following formula.

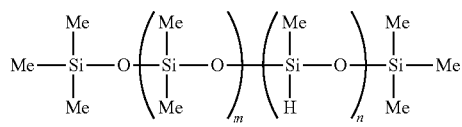

(4)

In the methylhydrogenpolysiloxane or dimethylmethylhydrogenpolysiloxane, SiH groups react on the powder surface to deactivate the powder surface. When the powder is incorporated in cosmetic, however, it sometimes degrades other components of the cosmetic. Further, the powder surface is not sufficiently deactivated.

Japanese Patent Application Laid-Open No. 2001-72891 describes a powder treating agent having a branched siloxane moiety. A catalyst to form the branch, however, tends to remain in the agent, causing increase in viscosity of the agent during storage.

SUMMARY OF THE INVENTION

An object of the present invention is to provide powder treated with an organopolysiloxane that is highly reactive with active groups on powder surface and is storage-stable.

Thus, the present invention is powder treated with a powder treating agent comprising organohydrogenpolysiloxane, characterized in that the organohydrogenpolysiloxane has a weight average molecular weight of from 300 to 100,000, at least one SiH bond per molecule, and at least one selected from $(R^1SiO_{3/2})$ unit and $(SiO_2)$ unit, wherein $R^1$ is selected from the group consisting of a hydrogen atom, and alkyl, fluorinated alkyl, aryl and aralkyl groups each having 1 to 30 carbon atoms.

The surface treating agent used in the present invention comprises an organopolysiloxane which has a branched structure, so that it covers powder surface two-dimensionally to deactivate surface better than a linear organopolysiloxane does. There are less residual SiH groups and hardly generate hydrogen gas during storage. Further, the organopolysiloxane is not prepared by addition-reaction of a silicone having terminal unsaturated groups with SiH, so that there is no formation of hydrogen gas or change in with time such as increase in viscosity due to remaining addition catalyst. In cosmetic containing the powder treated with the surface treating agent, the powder is very well dispersed. The cosmetic is stable with time and spreads smoothly on the skin.

DESCRIPTION OF THE PREFERRED EMBODIMENTS

The organopolysiloxane contained in the surface treating agent used in the present invention has a weight average molecular weight reduced to polystyrene of from 300 to 100,000, preferably from 500 to 10,000. An organohydrogenpolysiloxane having a weight average molecular weight larger than the aforesaid upper limit has higher viscosity and cosmetic containing powder treated with such an organohydrogenpolysiloxane may not be comfortable to use. On the other hand, an organohydrogenpolysiloxane having a weight average molecular weight smaller than the aforesaid lower limit tends to be unable to provide smoothness to powder surface. The weight average molecular weight can be determined by gel permeation chromatography (GPC).

Preferably, the organopolysiloxane has a viscosity of 10000 mm²/sec or smaller, more preferably of 5000 mm²/sec or smaller, and most preferably of 500 mm²/sec or smaller at 25° C. There is no lower limit of the viscosity, but a viscosity corresponding to the aforesaid lower limit of an average molecular weight usually ranges from 1 to 10 mm²/sec.

The organohydrogenpolysiloxane has at least one, preferable at least three, SiH bonds per molecule on average. An organohydrogenpolysiloxane having SiH bond less than the aforesaid lower limit is not sufficiently reactive with powder surface. An upper limit of a number of SiH bond per molecule is set according to reactivity of powder to be treated, but generally ranges from 5 to 50 per molecule. SiH bond may exist at any site in a molecule, preferably in $(R^2_3SiO_{1/2})$ unit or $(R^2_2SiO)$ unit.

The organohydrogenpolysiloxane contains at least one selected from $(R^1SiO_{3/2})$ unit, hereinafter referred to as T-unit, and $(SiO_2)$ unit, hereinafter referred to as Q-unit. It may have solely T-unit or Q-unit, but must have one of them. The T-unit is represented by the following formula (2), and Q-unit is by the formula (3). In the formulae, a bond extending from oxygen atom is bonded to other Si atom. Preferably, a total number of T-units and Q-units is ten or smaller. More preferably, the organohydrogenpolysiloxane contains 1 to 5 T-units and 0 to 3 Q-units.

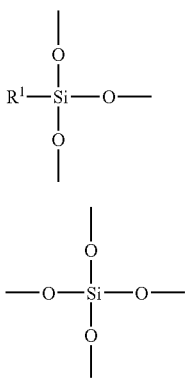

In the above formulae, $R^1$ is selected from a hydrogen atom and alkyl, fluorinated alkyl, aryl and aralkyl groups having 1 to 30 carbon atoms. When a plurality of T-units are contained, a plurality of $R^1$'s may be different with other. Examples of $R^1$ include alkyl groups such as methyl, ethyl, propyl, butyl, pentyl, hexyl, heptyl, octyl, nonyl and decyl groups; cycloalkyl groups such as cyclopentyl and cyclohexyl groups; aryl groups such as phenyl and tolyl groups; aralkyl groups such as benzyl and phenetyl groups; alcohol residues such as oleoyloxy and allyloxy groups; and fluorinated alkyl groups such as trifluoropropyl and heptadecafluorodecyl groups. Preferably, $R^1$ is a hydrogen atom, methyl, ethyl, octyl, nonyl, phenyl or trifluoropropyl group.

So-called a silicone network resin containing aforesaid T- and Q-units are conventionally used for cosmetics. However, they are used for forming film on the skin or hair and not for treating powder. Further, to attain the above object these resins do not have reactive groups in order not to change with time in the cosmetic nor affect other materials in the cosmetics.

Preferably, the organopolysiloxane used in the present invention is represented by the following average compositional formula (1):

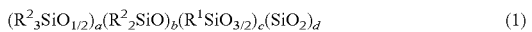

$$(R^2{}_3SiO_{1/2})_a(R^2{}_2SiO)_b(R^1SiO_{3/2})_c(SiO_2)_d \quad (1)$$

The above formula (1) represents structural units and average numbers thereof where different numbers of the units may be bonded randomly. In the formula, $(R^1SiO_{3/2})$ unit is the aforesaid T-unit, and $(SiO_2)$ is the aforesaid Q-unit. $R^2$, which may be different from each other, is selected from alkyl, fluorinated alkyl, aryl and aralkyl groups each having 1 to 30 carbon atoms. Examples of $R^2$ include those listed above for $R^1$ among which methyl, ethyl, octyl, nonyl, phenyl, and trifluoropropyl groups are preferred. In the formula (1), c and d are as defined above for the numbers of T-unit and Q-unit, respectively; a and b are such numbers that a weight average molecular weight of the organohydrogenpolysiloxane ranges from 300 to 100000. Typically, a ranges from 2 to 50, particularly from 2 to 20, and b ranges from 0 to 1000, particularly from 5 to 100.

The organopolysiloxane can be prepared by subjecting raw materials selected from those described below to hydrolysis and condensation reactions in the presence of acidic catalyst. The raw materials include silanes having $(R^2{}_3SiO_{1/2})$ unit, herein after referred to as M-unit, such as trimethylmethoxysilane, trimethylethoxysilane, and hexamethyldisiloxane; SiH bond-containing siloxanes such as tetramethylcyclotetrasiloxane; T-unit containing silanes and siloxanes such as tris(trimethylsiloxy)methylsilane, trimethoxymethylsilane, triethoxymethylsilane, hexyltrimethoxysilane, and octyltriethoxysilane; Q-unit containing silanes and siloxane such as tetramethoxysilane, and tetraethoxysilane; optionally, silanes containing $(R^2{}_2SiO)$ unit, hereinafter referred to as D-unit, and cyclic siloxanes such as dimethyldimethoxysilane, diethoxydimethylsilane, hexamethylcyclotrisiloxane, octamethylcyclosiloxane, decamethylcyclopentasiloxane, tris(trifluoropropyl)trimethylcyclotrisiloxane, and octaphenylcyclosiloxane.

Powder treatment with a powder treating agent comprising the organopolysiloxane can be performed by any known wet or dry method, for example, those as shown below:

1. Powder is mixed with a treating agent and then allowed to be treated in a mill such as a ball mill or jet mill.
2. A treating agent is mixed with a solvent, to which powder is added and dispersed, and then the solvent is dried.
3. A treating agent, which may be in the form of emulsion, is added to an aqueous slurry of powder and allowed to adsorb on the powder surface, and then the powder is dried.

In the aforesaid treatment method, the organopolysiloxane is used in an amount preferably of from 0.1 to 30 parts by weight, particularly from 0.5 to 10 parts by weight, per 100 parts by weight of powder.

The powder which can be treated with the treating agent comprising the organopolysiloxane is any powder which is commonly used in cosmetics, regardless of its shape such as spherical, needle or plate, its particle diameter such as fume, fine particle, or pigment grade, and its particle structure such as porous or non-porous. Examples of the powder or the coloring agent include inorganic powder, organic powder, powder of metal salts of surfactants, colored pigments, pearl pigments, metallic powder pigments, and natural colors.

Examples of the inorganic powder include titanium dioxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, metal salts of tungstenic acid, hydroxyapatite, vermiculite, higilite, bentonite, montmorillonite, hectoliter, zeolite, ceramics powder, calcium secondary phosphate, alumina, aluminum hydroxide, boron nitride, and silica.

Examples of the organic powder include polyamide powder, polyester powder, polyethylene powder, polypropylene powder, polystyrene powder, polyurethane powder, benzoguanamine powder, polymethylbenzoguanamine powder, tetrafluoroethylene powder, polymethylmethacrylate powder, cellulose powder, silk powder, powder of nylon such as Nylon 12 and Nylon 6, fine powder of crosslinked silicone with crosslinked dimethylsilicone structure, block copolymers of crosslinked silicone and network structure silicone, fine powder of polymethylsesquioxane, powder of styrene/acrylic acid copolymer, divinylbenzene/styrene copolymer, vinyl resin, urea resin, phenol resin, fluororesin, silicone resin, acrylic resin, melamine resin, epoxy resin, polycarbonate resin, microcrystalline fiber, starch powder, and lauroyl lysine.

Examples of the powder of metal salts of surfactants, i.e. metal soaps, include zinc stearate, aluminum stearate, calcium stearate, magnesium stearate, zinc myristate, magnesium myristate, zinc cetyl phosphate, calcium cetyl phosphate, and zinc sodium cetyl phosphate. Examples of the colored pigments include inorganic red pigments such as iron oxide, iron hydroxide, and iron titanate, inorganic brown pigments such as γ-iron oxide, inorganic yellow pigments such as iron oxide yellow and loess, inorganic black pigments such as iron oxide black and carbon black, inorganic violet pigments such as manganese violet and cobalt violet, inorganic green pigments such as chromium hydroxide, chromium oxide, cobalt oxide, and cobalt titanate, inorganic blue pigments such as Prussian blue and ultramarine blue, lakes of tar pigments, lakes of natural dyes, and synthetic resin powder, composite thereof.

Examples of the pearl pigments include titanium dioxide-coated mica, bismuth oxychloride, titanium dioxide-coated bismuth oxychloride, titanium dioxide-coated talc, fish scales, and titanium dioxide-coated colored mica; metallic powder pigments such as aluminum powder, copper powder and stainless steel powder; tar pigments such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207; and natural pigments such as carminic acid, laccaic acid, carthamin, brazilin, and crocin.

Powder treated with the present treating agent, hereinafter referred to the powder (A), is suitable for cosmetic. A content of the powder (A) is preferably adjusted according to kind and form of a cosmetic and properties of the powder. Typically the content is 0.1 to 70 wt %, preferably from 1 to 50 wt %, more preferably from 1 to 40 wt %, based on a total weight of a cosmetic.

Depending on the aim of the cosmetic according to the present invention, the cosmetic can contain one or more unctuous agents (B), which is commonly used for cosmetics and may be solid, semisolid, or liquid.

Examples of the natural animal or plant oils and semisynthetic oils which can be used as (B) include avocado oil, linseed oil, almond oil, Ibota wax, perilla oil, olive oil, cacao butter, kapok wax, kaya oil, carnauba wax, liver oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, camellia kissi seed oil, safflower oil, shear butter, Chinese tung oil, cinnamon oil, jojoba wax, shellac wax, turtle oil, soybean oil, tea seed oil, camellia oil, evening primrose oil, corn oil, lard, rapeseed oil, Japanese tung oil, rice bran oil, germ oil, horse fat, persic oil, palm oil, palm kernel oil, castor oil, hydrogenated castor oil, castor oil fatty acid methyl ester, sunflower oil, grape oil, bayberry wax, jojoba oil, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, hydrogenated lanolin, lanolin alcohol, hard lanolin, lanolin acetate, isopropyl lanolate, hexyl laurate, POE lanolin alcohol ether, POE lanolin alcohol acetate, polyethylene glycol lanolate, POE hydrogenated lanolin alcohol ether, and egg yolk oil, wherein POE means polyoxyethylene.

Examples of the hydrocarbon oils which can be used as (B) include ozokerite, squalane, squalene, ceresin, paraffin, paraffin wax, liquid paraffin, pristane, polyisobutylene, microcrystalline wax, vaseline and higher fatty acids, e.g., lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid.

Examples of the higher alcohols which can be used as (B) include lauryl alcohol, myristyl alcohol, palmityl alcohol, stearyl alcohol, behenyl alcohol, hexadecyl alcohol, oleyl alcohol, isostearyl alcohol, hexyldodecanol, octyl dodecanol, cetostearyl alcohol, 2-decyltetradecinol, cholesterol, phytosterol, POE cholesterol ether, monostearyl glycerin ether (batyl alcohol), and monooleyl glyceryl ether (cerakyl alcohol).

Examples of the ester oils which can be used as (B) include diisobutyl adipate, 2-hexyldecyl adipate, di-2-heptylundecyl adipate, N-alkyl glycol monoisostearate, isocetyl isostearate, trimethylolpropane triisostearate, isononyl isononanate, isotridecyl isononanate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprirate, triethyl citrate, 2-ethylhexyl succinate, amyl acetate, ethyl acetate, butyl acetate, isocetyl stearate, butyl stearate, diisopropyl sebacinate, di-2-ethylhexyl sebacinate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, and diisostearyl malate; and glyceride oils, e.g., acetoglyceryl, glycerol triisooctanoate, glyceryl triisostearate, glyceryl triisopalmitate, glyceryl monostearate, glyceryl di-2-heptylundecanoate, glyceryl trimyristate, and diglyceryl myristyl isostearate.

Examples of the silicone oils which can be used as (B) include organopolysiloxanes having a low or high viscosity, such as dimethylpolysiloxane, methylphenylpolysiloxane, methylhydrogenpolysiloxane and dimethylsiloxane-methylphenylsiloxane copolymer; cyclosiloxanes, such as octamethylcyclotetrasiloxane, decamethylcyclopentasiloxane, dodecamethylcyclohexasiloxane, tetramethyltetrahydrogencyclotetrasiloxane and tetramethyl-tetraphenylcyclotetrasiloxane, tetramethyltetretrifluoropropyl cyclotetrasiloxane pentamethyltrifluoropropyl cyclopentasiloxane; silicone rubbers, such as gummy dimethylpolysiloxanes and gummy dimethylsiloxane-methylphenylsiloxane copolymers having high polymerization degrees; solutions of silicone rubbers in cyclosiloxane, trimethylsiloxysilicate, solutions of trimethylsiloxysilicate in cyclosiloxane, higher alkyl-modified silicones such as stearoxysilicone, alkyl-modified silicones, amino-modified silicones, fluorine-modified silicones, silicone resin and silicone resin solutions. Examples of the fluorine-containing oils which can be used as (B) include perfluoropolyether, perfluorodecalin and perfluorooctane.

Preferably, at least a part of the unctuous agent (B) is a linear or cyclic silicone oil represented by the following formula:

$$R^3_k SiO_{(4-k)/2}$$

wherein $R^3$ is selected from a hydrogen atom, and alkyl, aryl, aralkyl, and fluorinated alkyl groups each having 1 to 30 carbon atoms and k is the number of from 0 to 2.5.

The unctuous agent (B) can be incorporated in the cosmetic in an amount of from 1 to 98 wt % based on the total weight of the cosmetic.

The cosmetics according to the present invention may contain water (C), depending on the aim of cosmetics. Suitable mixing ratio is 1 to 95 wt.% of the total cosmetics, depending on the form of the cosmetics.

The cosmetics according to the present invention may contain one or more compounds having an alcoholic hydroxyl group in the molecular structure (D), depending on the aim of cosmetics. Examples of the compounds having an alcoholic hydroxyl group include lower alcohols such as ethanol and isopropanol; sugar alcohols such as sorbitol and maltose; sterols such as cholesterol, sitosterol, phytosterol, and lanosterol; and polyhydric alcohol such as glucose, butylene glycol, propylene glycol, dibuthylene glycol, and pentylene glycol. A desirable added amount ranges from 0.1 to 98 wt.% based on the total cosmetics.

Depending on an intended use of cosmetic, the cosmetic according to the present invention may preferably contain one or more water-soluble or water-swelling polymer (E). Examples of such polymer include plant polymers such as gum Arabic, tragacanth gum, arabinogalactan, guar gum, karaya gum, carrageenan, pectin, agar, quince seed (i.e., marmelo), starch from rice, corn, potato or wheat, algae colloid, trant gum, and locust bean gum (carob gum); bacteria-derived polymers such as xanthan gum, dextran, succinoglucan, and pullulan; animal-derived polymers such as collagen, casein, albumin, and gelatin; starch-derived polymers such as carboxymethyl starch and methylhydroxypropyl starch; cellulose polymers such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose powder; alginic acid-derived polymers such as sodium alginate and propylene glycol alginate; vinyl polymers such as polyvinyl methylether, polyvinylpyrrolidone, and carboxyvinyl polymer; polyoxyethylene polymers such as polyoxyethylene/polyoxypropylene copolymers; acrylic polymers such as sodium polyacrylate, polyethyl acrylate, and polyacrylamide; other synthetic water-soluble polymers such as polyethyleneimine and cationic polymers; and inorganic water-soluble polymers such as, bentonite, aluminum magnesium silicate, montmorilonite, beidellite, nontronite, saponite, hectorite, and silicic anhydride. In these water-soluble polymers, film-forming agents, such as polyvinyl alcohol and polyvinyl pyrrolidine, are also included. Suitable amount to be contained is 0.1 to 25 wt.%, based on the total cosmetics.

In the present invention, powder other than the powder (A) may be used. Any powder that are commonly used in cosmetics can be used, regardless of the shape such as spherical, needle or plate, particle diameter such as fume, fine particle, or pigment grade, and particle structure such as porous or non-porous. Examples of the powder include inorganic powder, organic powder, metal salt powder of surfactant, colored pigments, pearl pigments, metallic powder pigments, and natural colors.

Examples of the powder include those already mentioned above for the powder (A). The powder may be the composite powder or powder which has been treated with general oil, silicone oil, fluorinated compounds, or surfactants as long as such treatment does not prevent the effect of the present invention and one or more kinds of these powders may be used. Suitable amount to be used is 0.1 to 99 wt.%, based on the total cosmetics. Especially for pressed powder cosmetics, suitable amount is 80 to 99 wt.% based on the total cosmetics.

The cosmetics according to the present invention may comprise one kind or two or more kinds of surfactant (G), depending on the aim of cosmetics. These surfactants have no particular restriction and may be any surfactants of anionic, cationic, nonionic or amphoteric surfactant, provided that it is commonly used in cosmetics.

Examples of the anionic surfactants include fatty acid soaps, such as sodium stearate and triethanolamine palmitate, alkylether carboxylic acids and salts thereof, salts of condensates of amino acids with fatty acids, alkyl sulfonate salts, alkenesulfonates, sulfonates of fatty acid esters, fatty acid amide sulfonates, sulfonate salts of the formalin condensates, salts of alkyl sulfates, salts of secondary higher alcohol sulfates, salts of alkyl/allyl ether sulfates, salts of fatty acid ester sulfates, salts of fatty acid alkylolamide sulfates, and salts of Turkey Red oil salfate, alkyl phosphate salts, ether phosphate salts, alkylallylether phosphate salts, amide phosphate salts, and N-acylamino surfactants; the cationic surfactants include amine salts such as alkylamine salts, amine salts of polyamine and amino alcohol fatty acid derivatives, alkyl quaternary ammonium salts, aromatic quaternary ammonium salts, pyridinium salts and imidazolium salts.

Examples of the nonionic surfactants include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ether, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, linear or branched-polyoxyalkylene-modified organopolysiloxane, linear or branched polyoxyalkylene/alkyl-comodified organopolysiloxane, linear or branched-polyglycerin-modified organopolysiloxane, linear or branched-polyglycerin/alkyl-comodified organopolysiloxane, alkanolamide, sugar ethers, and sugar amides; and the amphoteric surfactants include betaine, aminocarboxylates, imidazoline derivatives, and amide amine type. A suitable amount of the surfactant to be added ranges from 0.1 to 20 wt. %, particularly preferably from 0.2 to 10 wt. % relative to the total amount of the cosmetic.

The cosmetic according to the present invention may contain one or more crosslinked organopolysiloxane (H) other than the aforesaid crosslinked silicone powder. Preferably, the organopolysiloxane (H) swells by absorbing silicone with a viscosity of from 0.65 mm$^2$/sec to 10.0 mm$^2$/sec at 25° C. in an amount larger than or equal to the weight of the crosslinked polyorganosilixane itself. Preferably, crosslinkage of the organopolysiloxane (H) has alkylene groups having 2 to 5 carbon atoms at both ends. The alkylene groups can be derived by reacting diallyl compounds with SiH bonds. Preferably, the crosslinkage further has at least one group selected from the moeity consisting of polyglycerin residue, alkyl group, alkylene group, aryl group, arylene group, fluoroalkyl group and fluroalkylene group. The crosslinked organopolysiloxane (H) is incorporated in the cosmetic in an amount preferably of from 0.1 to 50 wt %, more preferably of from 1 to 30 wt % based on a total weight of the cosmetic.

Additionally, this crosslinked organopolysiloxane preferably can absorb a larger amount of oil than that of itself to swell. Examples of the oils include silicone with a low viscosity from 0.65 mm$^2$/sec to 10.0 mm$^2$/sec, hydrocarbon oils and ester oils. It is also preferred to use a crosslinked organopolysiloxane containing, in the crosslinked molecule, at least a moiety selected from a group consisting of polyoxyalkylene, alkyl, alkenyl, aryl, and fluoroalkyl moieties.

Suitable amount of crosslinked organopolysiloxane to be added is preferably 0.1 to So wt. %, more preferably 1to 30 wt. %, based on the total cosmetics.

The cosmetic according to the present invention may contain one or more silicone resins selected from the group consisting of acrylic silicone resin and silicone network resin expressed as MQ, MDQ, MT, MDT, and MDTQ. The acrylic silicone resin may be acrylic silicone graft polymer or block polymer. The units, M, D, T and Q are as defined above. These network silicone resin do not has SiH bond. Preferably, the acrylic silicone resin and the network silicone resin has at least one moiety selected from the group consisting of pyrrolidone residue, long chain alkyl group, polyoxyalkylene group, fluoroalkyl group, carboxylic group and amino group. The acrylic silicone resin and the network silicone resin is incorporated in the cosmetic in an amount of from 0.1 to 20 wt. %, more preferably from 1 to 10 wt. %, based on the total cosmetic.

In the cosmetic of the present invention, a variety of components that are commonly used in cosmetics can be blended in addition to the aforementioned components, as far as the purpose of the present invention is not damaged, for example, oil-soluble gelling agents, clay minerals modified with organic compounds, resins, antiperspirants, ultraviolet absorbents, ultraviolet absorbing and scattering agents, moisture retention agents, antiseptics, anti-microbial agents, fragrances, salts, antioxidants, pH regulators, a chelating agents, refreshing agents, an anti-inflammatory agent, skin beautifying components, such as skin whitener, cell activator, rough dry skin improver, blood circulation promoter, skin astringent and anti-seborrheic agent, vitamins, amino acids, nucleic acids, hormones, clathrate compounds, and hair setting agents The oil-soluble gelling agent may be a gelling agent selected from metal soaps, such as aluminum stearate, magnesium stearate and zinc myristate; amino acid derivatives, such as N-lauroyl-L-glutamic acid and α,γ-di-n-butylamine; dextrin fatty acid esters, such as dextrin palmitic acid ester, dextrin stearic acid ester and dextrin 2-ethylhexaminic acid palmitic acid ester; inulin fatty acid esters such as fructooligostearate; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay.

Examples of the antiperspirant include aluminum chlorohydrate, aluminum chloride, aluminum sesquichlorohydrate, zirconium hydoxychloride, aluminum zirconium hydroxychloride, and aluminum zirconium glycine complex.

Examples of the ultraviolet absorbents include ultraviolet absorbents of benzoic acid type, such as p-aminobenzoic acid; those of anthranilic acid type, such as methyl anthranilate; those of salicylic acid type, such as methyl salicylate; those of succinic acid type, such as octyl p-methoxysuccinate; those of benzophenone type, such as 2,4-dihydroxybenzophenone; those of urocanic acid type, such as ethyl urocanate; and those of dibenzoylmethane type, such as 4-t-butyl-4'-methoxydibenzoylmethane. Examples of the ultraviolet absorbing and scattering agents include fine powder of titanium dioxide, fine powder of iron-containing titanium dioxide, fine powder of zinc oxide, fine powder of cerium oxide, and a mixture thereof.

Examples of the moisture retention agents include glycerin, sorbitol, propylene glycol, dipropylene glycol, 1,3-butylene glycol, pentylene glycol, glucose, xylitol, maltitol, polyethylene glycol, hyaluronic acid, chondroitin sulfuric acid, pyrrolidone carboxylate, polyoxyethylene glycoside, and polyoxypropylene methylglycoside.

For the antiseptics, alkyl paraoxybenzoates, benzoic acid, sodium benzoate, sorbic acid, potassium sorbate, and phenoxyethanol may be used. For the antibacterial agents, benzoic acid, salicylic acid, carbolic acid, sorbic acid, paraoxybenzoic acid alkyl esters, parachloromethacresol, hexachlorophene, benzalkonium chloride, chlorohexydine chloride, trichlorocarbanilide and phenoxyethanol.

Examples of the antioxidants include tocopherol, butylhydroxyanisole, dibutylhydroxytoluene and phytic acid; examples of the pH regulators include lactic acid, citric acid, glycolic acid, succinic acid, tartaric acid, dl-malic acid, potassium carbonate, sodium hydrogen carbonate and ammonium hydrogen carbonate; examples of the chelating agents include alanine, sodium ethylenediaminetetraacetate, sodium polyphosphate, sodium metaphosphate and phosphoric acid; examples of the refrigerants include L-menthol and camphor; and examples of the anti-inflammatory agents include allantoin, glycyrrhizin and salts thereof, glycyrrhetinic acid and stearyl glycyrrhetinate, tranexamic acid and azulene.

Examples of the skin-beautifying components include whitening agents, such as placenta extract, arbutin, glutathione and Yukinoshita extract; cell activators, such as royal jelly, photosensitizers, cholesterol derivatives and calf blood extract; rough and dry skin improvers; blood circulation improvers, such as nonylic acid vanillyl amide, benzyl nicotinate, beta-butoxyethyl nicotinate, capsaicin, zingerone, cantharis tincture, ichtammol, caffeine, tannic acid, alpha-borneol, tocopheryl nicotinate, inositol hexanicotinate, cyclandelate, cinnarizine, tolazoline, acetyl choline, verapamil, cepharanthin and gamma-oryzanol; skin astringents, such as zinc oxide and tannic acid; and anti-seborrheic agents, such as sulfur and thianthol.

Examples of the vitamins include vitamin A, such as vitamin A oil, retinol, retinyl acetate and retinyl palmitate; vitamin B, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin B15 and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as alpha-tocopherol, beta-tocopherol, gamma-tocopherol, dl-alpha-tocopheryl acetate, dl-alpha-tocopheryl nicotinate and dl-alpha-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of the amino acids include glycine, valine, leucine, isoleucine, serine, threonine, phenylaranine, alginine, lysine, aspartic acid, glutamic acid, cystine, cysteine, methionine, and tryptophan; examples of the nucleic acids include deoxyribonucleic acid; and examples of the hormones include estradiol and ethenyl estradiol.

Examples of the polymers for hair setting include amphoteric, anionic, cationic, and nonionic polymers, such as polymers of polyvinyl pyrrolidone type such as polyvinyl pyrrolidone, vinyl pyrrolidone/vinyl acetate copolymers; acidic polymers of vinyl acetate ether type such as methyl vinyl ether/maleic acid anhydride alkyl half ester copolymer; polymers of acidic poly vinyl acetate type such as vinyl acetate/crotonic acid copolymer; acidic acrylic polymers such as (meth)acrylic acid/alkyl(meth)acrylate copolymer, (meth)acrylic acid/alkyl(meth)acrylate/alkyl acrylic amide copolymer, and amphoteric acrylic polymer such as N-methacryloylethyl-N,N-dimethylammonium alpha-N- methylcarboxybetaine/alkylmetahcrylate copolymer, hydroxypropyl(metha)acrylate/butylaminoethyl methacrylate/octyl amide of acrylic acid copolymer. Use is also made of naturally occurring polymers such as cellulose or derivatives thereof, keratin, collagen and derivatives thereof.

The present cosmetic may be various types of cosmetic such as face lotion, milky lotion, cream, face cleansing cream, massage materials, toilet soap and detergent, antiperspirant and deodorant; makeup products, such as face powder, foundation, rouge, eye shadow, mascara, eyeliner and lipstick; and hairdressing products, such as shampoo, rinse, treatment setting agent, antipersipirant and ultraviolet protection cosmetics, such as sunscreen milky lotion or sunscreen cream.

The present cosmetic materials may have various forms such as liquid, emulsion, solid, paste, gel, powder, press, laminate, mousse, spray, stick, pencil forms.

EXAMPLES

The present invention will be further explained below with reference to the Examples, but not limited thereto. In the followings, "%" means "% by weight" unless otherwise specified.

Example 1

In a reactor, 31 parts by weight of tris(trimethylsiloxy) methyl silane, 74 parts by weight of octamethylcyclotetrasiloxane, and 30 parts by weight of tetramethylcyclotetrasiloxane were placed, to which 8.3 parts by weight of concentrated sulfuric acid was added. A mixture obtained was stirred at room temperature for 5 hours. A reaction mixture obtained was washed with water and then unreacted silane and siloxane were distilled off. An organohydrogenpolysiloxane of the following average compositional formula (5) was obtained.

$$[(CH_3)_3SiO_{1/2}]_3[(CH_3)_2SiO]_{10}[(CH_3)HSiO]_5[CH_3SiO_{3/2}]_1 \quad (5)$$

This reaction product was colorless and transparent liquid having a viscosity of 25 mm²/s at 25° C.

Example 2

In a reactor, 32.4 parts by weight of hexamethyldisiloxane, 55.2 parts by weight of octyltriethoxysilane, 222 parts by weight of octamethylcyclotetrasiloxane and 60 parts by weight of tetramethylcyclotetrasiloxane were placed, to which 19.3 parts by weight of concentrated sulfuric acid and 5.4 parts by weight of water was added. A mixture obtained was stirred at room temperature for 10 hours. A reaction mixture obtained was washed with water and then unreacted silane and siloxane were distilled off. An organohydrogenpolysiloxane of the following average compositional formula (6) was obtained.

$$[(CH_3)_3SiO_{1/2}]_3[(CH_3)_2SiO]_{30}[(CH_3)HSiO]_{10}[C_8H_{17}SiO_{3/2}]_2 \quad (6)$$

This reaction product was colorless and transparent liquid having a viscosity of 42 mm²/s at 25° C.

Example 3

In a reactor, 32.4 parts by weight of hexamethyldisiloxane, 55.2 parts by weight of octyltriethoxysilane, 180 parts by weight of tetramethylcyclotetrasiloxane and 37.8 parts by weight of tris(trifluoropropyl)trimethylcyclotrisiloxane were placed, to which 15 parts by weight of concentrated sulfuric acid and 5.4 parts by weight of water was added. A mixture obtained was stirred at room temperature for 10 hours. A reaction mixture obtained was washed with water and then unreacted silane and siloxane were distilled off. An organohydrogenpolysiloxane of the following average compositional formula (7) was obtained.

$$[(CH_3)_3SiO_{1/2}]_3[(CH_3)(CF_3C_2H_4)SiO]_3[(CH_3)HSiO]_{30}[C_8H_{17}SiO_{3/2}]_2 \quad (7)$$

This reaction product was colorless and transparent liquid having a viscosity of 34 mm²/s at 25° C.

Example 4

In a reactor, 32.4 parts by weight of hexamethyldisiloxane, 20.8 parts by weight of tetraethoxysilane, 148 parts by weight of octamethylcyclotetrasiloxane and 60 parts by weight of tetramethylcyclotetrasiloxane were placed, to which 13 parts by weight of concentrated sulfuric acid and 7.2 parts by weight of water was added. A mixture obtained was stirred at room temperature for 10 hours. A reaction mixture obtained was washed with water and then unreacted silane and siloxane were distilled off. An organohydrogenpolysiloxane of the following average compositional formula (8) was obtained.

$$[(CH_3)_3SiO_{1/2}]_4[(CH_3)_2SiO]_{20}[(CH_3)HSiO]_{10}[SiO_2] \quad (8)$$

This reaction product was colorless and transparent liquid having a viscosity of 32 mm²/s at 25° C.

Example 5

In a reactor, 48.6 parts by weight of hexamethyldisiloxane, 55.2 parts by weight of octyltriethoxysilane, 60 parts by weight of tetramethylcyclotetrasiloxane and 222 parts by weight of octamethylcyclotetrasiloxane were placed, to which 19 parts by weight of concentrated sulfuric acid and 5.4 parts by weight of water was added. A mixture obtained was stirred at room temperature for 10 hours. A reaction mixture obtained was washed with water and then unreacted silane and siloxane were distilled off. An organohydrogenpolysiloxane of the following average compositional formula (9) was obtained.

$$[(CH_3)_3SiO_{1/2}]_6[(CH_3)_2SiO]_{30}[(CH_3)HSiO]_{10}[C_8H_{17}SiO_{3/2}]_2[SiO_2] \quad (9)$$

This reaction product was colorless and transparent liquid having a viscosity of 58 mm²/s at 25° C.

Examples 6 to 11, Comparative Examples 1 and 2

Powder was treated with the organopolysiloxane powder treating agents prepared in Examples 1 to 3, and a linear dimethylhydrogenpolysiloxane, herein after referred to as "treating agent 1", respectively, according to the formulations shown in Table 1 where numerals are given in parts by weight.

TABLE 1

| Example No. | Powder | | Treating agent | | | |
| | Titanium oxide fine powder | Sericite | Example 1 | Example 2 | Example 3 | Treating agent 1 |
|---|---|---|---|---|---|---|
| Example 6 | 98 | | 2 | | | |
| Example 7 | 98 | | | 2 | | |
| Example 8 | 98 | | | | 2 | |
| Example 9 | | 95 | 5 | | | |
| Example 10 | | 95 | | 5 | | |
| Example 11 | | 95 | | | 5 | |

TABLE 1-continued

| Example No. | Powder | | Treating agent | | | |
| | Titanium oxide fine powder | Sericite | Example 1 | Example 2 | Example 3 | Treating agent 1 |
|---|---|---|---|---|---|---|
| Comparative Example 1 | 98 | | | | | 2 |
| Comparative Example 2 | | 95 | | | | 5 |

Treating agent 1: diimethylhydrogenpolysiloxane, KF9901, ex Shin-Etsu Chemical Co., Ltd.

Method of Treating Powder

Powder of titanium oxide and sericite were vacuum dried at 20 mmHg and at 150° C. for 1 hour. In a reactor, 98 parts by weight of the titanium oxide powder were placed, to which a solution of the powder treating agent was gradually added while stirring, which solution was prepared by diluting 2 or 5 parts by weight of the powder treating agent with toluene about 5 times. Then, toluene was evaporated by heating and the heating at 150° C. was kept for further 3 hours while stirring. In the same manner, 95 parts by weight of sericite were treated.

The powder thus treated was evaluated in terms of surface activity, water resistance, and generated hydrogen gas. The results are as shown in Table 2.

TABLE 2

| Treated Powder | Surface activity(ΔE) | Water resistance(hr) | Amount of generated hydrogen gas(cc/g) |
|---|---|---|---|
| Example 6 | 0.8 | 3.0 | 0.5 |
| Example 7 | 0.9 | 3.5 | 0.4 |
| Example 8 | 1.0 | 3.5 | 0.4 |
| Example 9 | 0.2 | 3.0 | 1.0 |
| Example 10 | 0.3 | 3.5 | 0.9 |
| Example 11 | 0.3 | 3.5 | 0.9 |
| Comparative Example 1 | 1.8 | 3.0 | 1.9 |
| Comparative Example 2 | 1.2 | 2.5 | 2.5 |

Method of Evaluation (1) Surface Activity

The treated powder in an amount of 40 parts by weight were mixed with 60 parts by weight of castor oil. A predetermined amount of the mixture was sandwiched between glass plates and then irradiated with UV light for a predetermined time. Difference in color of the powder was measured with a color-difference meter. A difference in color implies larger surface activity.

(2) Water Resistance

A predetermined amount of the treated powder was pressed in a 50 mm Φ aluminum plate. Around the center of a surface of the powder disc thus obtained a drop of a blend of 1,3-butyleneglycol and water in 1:1 volume ratio was placed and a period of time required for the drop to penetrate in the disc was measured. A longer period of time means a higher water resistance.

(3) Amount of Generated Hydrogen Gas

This is to measure an amount of residual SiH bonds on powder surface. A predetermined amount of powder was dispersed in toluene, in which 20% KOH solution was dropped. A volume of generated hydrogen gas was measured.

As shown in Table 2, the powder of Examples 6, 7 and 8 showed color difference smaller than that of the powder of Comparative Example 1 and the powder of Examples 9, 10 and 11 showed color difference smaller than that of the powder of Comparative Example 2. The organopolysiloxanes used in the present invention were found to deactivate powder surface more effectively than the linear dimethylhydrogenpolysiloxane. The powder of Comparative Examples 1 and 2 showed tolerable water resistance, but generated large amount of hydrogen gas, indicating large amount of residual SiH bonds. The powders of Examples 6 to 11 showed good water resistance and generated less hydrogen gas.

Examples 12 to 14, Comparative Example 3

Using the powders of Examples 6 to 11, and Comparative Examples 1 and 2, foundation was prepared according to the formulations shown below.

TABLE 3

| | Component | Formulation(parts by weight) | | | |
| | | Ex*1. 12 | Ex. 13 | Ex. 14 | Comp. Ex*2. 3 |
|---|---|---|---|---|---|
| 1 | Titanium oxide of Example 6 | 12 | — | — | — |
| 2 | Sericite of Example 9 | 35 | — | — | — |
| 3 | Titanium oxide of Example 7 | — | 12 | — | — |
| 4 | Sericite of Example 10 | — | 35 | — | — |
| 5 | Titanium oxide of Example 8 | — | — | 12 | — |
| 6 | Sericite of Example 11 | — | — | 35 | — |
| 7 | Titanium oxide of Comparative Example 1 | — | — | — | 12 |
| 8 | Sericite of Comparative Example 2 | — | — | — | 35 |
| 9 | Talc treated with lecithin | 35.1 | 35.1 | 35.1 | 35.1 |
| 10 | Spherical Nylon powder treated with lecithin | 5 | 5 | 5 | 5 |
| 11 | Iron oxide red | 0.4 | 0.4 | 0.4 | 0.4 |
| 12 | Iron oxide yellow | 2 | 2 | 2 | 2 |
| 13 | Amber | 0.4 | 0.4 | 0.4 | 0.4 |
| 14 | Iron oxide black | 0.1 | 0.1 | 0.1 | 0.1 |
| 15 | Dimethylpolysiloxane (6 mm$^2$/sec at 25° C.) | 7 | 7 | 7 | 7 |
| 16 | Glyceryl trioctanoate | 1.5 | 1.5 | 1.5 | 1.5 |
| 17 | Dipentaerythritol fatty acid ester | 1.5 | 1.5 | 1.5 | 1.5 |

*[1]Ex. stands for Example.
*[2]Comp. Ex stands for Comparative Example.

Preparation Procedures

A: Components 1 to 14 were mixed uniformly and pulverized.

B: To the mixture thus obtained, components 15 to 17 were added and kneaded.

C: Powder foundation was obtained by press molded the product obtained in the step B.

The obtained foundation was rated concerning usability, spreadability, no smudge, and durability by 50 women panelists according to the following criteria.

Criteria for Rating 5 points: good 4 points: slightly good 3 points: ordinary 2 points: slightly bad 1 point: bad The ratings were averaged and evaluation results as shown in Table 4 were obtained according to the following criteria.

Criteria for Evaluation Results in Table 4

A: 4.5 or higher

B: 3.5 to less than 4.5

C: 2.5 to less than 3.5

D: 1.5 to less than 2.5

E: less than 1.5

TABLE 4

|  | Example 12 | Example 13 | Example 14 | Comp. Ex. 3 |
| --- | --- | --- | --- | --- |
| Usability | B | B | B | B |
| Spreadability | A | B | B | B |
| No smudge | B | A | A | C |
| Durability | A | A | A | C |

As is evident from Table 4, the foundation of Examples 12, 13 and 14 were superior to that of Comparative Example 3 in usability, spreadability, and durability.

After the step B in the aforesaid preparation procedures, a portion of the foundation of Comparative Example 3 was sampled and kept in a closed container. After 30 days, it was observed that the container bulged due to hydrogen gas generated by dehydrogenation reaction of residual SiH groups.

Examples of various cosmetic are shown below. Powder was treated in the same manner as in Example 6 unless otherwise specified. Stability with time was evaluated by visually inspecting change in appearance after keeping a cosmetic at 50° C. for 60 days.

Example 15

Oil-In-water Type Cream

| Component | Weight % |
| --- | --- |
| 1. Ethanol | 17.0 |
| 2. Propylene glycol | 3.0 |
| 3. Polyether-modified silicone[1] | 0.5 |
| 4. Glyceryl trioctanoate | 2.0 |
| 5. Sericite treated with the organopolysiloxane of Example 1 | 3.0 |
| 6. Composite powder of hybrid silicone[2] | 5.0 |
| 7. Carboxyvinyl polymer (1% aqueous solution) | 20.0 |
| 8. Xanthan gum (2% aqueous solution) | 6.0 |
| 9. Triethanolamine | 0.2 |
| 10. Antiseptics agent | q.s. |
| 11. Fragrance | q.s. |
| 12. Purified water | 60.8 |

[1]Polyether-modified silicone; KF-6011, from Shin-Etsu Chemical Co., Ltd.
[2]Composite powder of hybrid silicone; KSP-100, from Shin-Etsu Chemical Co., Ltd.

Preparation Procedures

A: Components 1 to 6 were mixed.

B: Components 7 to 12 were mixed to dissolve.

C: The mixture obtained in A was added to the mixture obtained in B and the resulting mixture was emulsified by stirring.

The oil-in-water type cream thus obtained had fine texture and was stable with time. It spread well on the skin and gave non-greasy and refreshing feel to the skin.

Example 16

Oil-In-Water Cream

| Component | Weight % |
| --- | --- |
| 1. Crosslinked dimethylpolysiloxane[1] | 10.0 |
| 2. Glyceryl trioctanoate | 5.0 |
| 3. Dipropylene glycol | 7.0 |
| 4. Glycerin | 5.0 |
| 5. Methyl cellulose (2% aqueous solution)[2] | 7.0 |
| 6. Emulsifier of polyacrylic amide type[3] | 2.0 |
| 7. Mica titanium treated with organopolysiloxane of Example 2 | 1.0 |
| 8. Antiseptics | q.s. |
| 9. Fragrance | q.s. |
| 10. Purified water | 63.0 |

[1]Crosslinked dimethylpolysiloxane; KSG-16 from Shin-Etsu Chemical Co., Ltd.
[2]Methyl cellulose; Metholose SM-4000 from Shin-Etsu Chemical Co., Ltd.
[3]Emulsifier of polyacrylic amide type; Sepigel 305 from SEPIC Preparation Procedures A: Components 3 to 10 were mixed.

B: Components 1 and 2 were mixed.

C: The mixture obtained in B was added to the mixture obtained in A and emulsified by stirring.

The Oil-in-water cream obtained had fine texture and was stable with time. It spread well on the skin and gave non-greasy and refreshing feel to the skin.

Example 17

Water-In-Oil Type Cream

| Component | Weight % |
| --- | --- |
| 1. Dimethylpolysiloxane (6 mm$^2$/sec at 25° C.) | 6.0 |
| 2. Methylphenylpolysiloxane | 4.0 |
| 3. Squalane | 5.0 |
| 4. Neopentylglycol dioctanoate | 3.0 |
| 5. Polyether-modified silicone[1] | 3.0 |
| 6. Fine particulate of hydrophobized titanium dioxide[2] | 2.0 |
| 7. Magnesium sulfate | 0.7 |
| 8. Glycerin | 10.0 |
| 9. Antiseptics | q.s. |
| 10. Fragrance | q.s. |
| 11. Purified water | balance |

[1]Polyether-modified silicone; KF 6012 from Shin-Etsu Co., Ltd.
[2]Fine particulate of hydrophobized titanium powder; fine particulate of titanium dioxide with average particulate diameter of 0.05 μm was dispersed in water so that the content of titanium would be 10 wt. %. Then 10 wt. % sodium silicate solution, where the molar ratio of SiO$_2$/Na$_2$O = 0.5, was added so that the SiO$_2$ content would be 2 wt. % relative to titanium dioxide and 10 wt. % aluminum sulfate solution was added dropwise so that the Al$_2$O$_3$ content would be 7.5 wt. % relative to titanium dioxide to deposit silicic acid hydrate and alumina hydrate on the surface of titanium dioxide. After the reaction was completed, the reactant was filtered, washed, dried and pulverized with the aid of jet mill. The resulting particulate was placed in Henschel mixer, 2 wt. % of organopolysiloxane of Example 3 was added while stirring sufficiently, the resulting mixture was mixed and stirred, and then was calcined at 120° C.

Preparation Procedures

A: Components 1 to 5 were mixed while heating, to which component 6 was added and was mixed.

B: Components 7 to 9 and 11 were mixed.

C: While stirring, the mixture obtained in B was added dropwise to the mixture A and was emulsified. Then, component 10 was added.

The water-in-oil cream obtained had fine texture and was stable with time. It spread well on the skin and gave non-greasy and refreshing feel to the skin.

Example 18

Water-In-Oil Type Cream

| Component | Weight % |
|---|---|
| 1. Alkyl-modified crosslinked polyether-modified silicone[1] | 6.0 |
| 2. Liquid paraffins | 13.5 |
| 3. *Macadamia* nuts oil | 5.0 |
| 4. Alkyl/polyether co-modified silicone[2] | 0.5 |
| 5. Composite powder of hybrid silicone[3] | 3.0 |
| 6. titanium dioxide treated with the organopolysiloxane of Example 4 | 2.0 |
| 7. Sodium citrate | 0.2 |
| 8. Propylene glycol | 8.0 |
| 9. Glycerin | 3.0 |
| 10. Antiseptics | q.s. |
| 11. Fragrance | q.s. |
| 12. Purified water | 58.8 |

[1] Alkyl-modified crosslinked polyether-modified silicone KSG-310 from Shin-Etsu Co., Ltd.
[2] Alkyl/polyether co-modified silicone; KF-6026 from Shin-Etsu Co., Ltd.
[3] Composite powder of hybrid silicone; KSP-100 from Shin-Etsu Co., Ltd.

Preparation Procedures
A: Components 1 to 6 were mixed.
B: Components 7 to 12 were mixed.
C: The mixture obtained in B was added to the one obtained in A and emulsified.

The water-in-oil cream obtained had fine texture and was stable with time. It spread well on the skin and gave non-greasy and refreshing feel to the skin.

Example 19

Water-In-Oil Type Cream

| Component | Weight % |
|---|---|
| 1. Decamethylcyclopentasiloxane | 16.0 |
| 2. Dimethylpolysiloxane (6 mm2/sec at 25° C.) | 4.0 |
| 3. Polyether-modified silicone[1] | 5.0 |
| 4. POE (5) octyl dodecyl ether | 1.0 |
| 5. Polyoxyethylene sorbitan monostearate (20E.O.) | 0.5 |
| 6. Zinc oxide treated with silicic anhydride[2] | 2.0 |
| 7. Titanium dioxide fine powder treated with the organopolysiloxane of Example 2 | 10.0 |
| 8. Liquid paraffins | 2.0 |
| 9. *Macadamia* nuts oil | 1.0 |
| 10. *Scuttellaria* Root Extract[3] | 1.0 |
| 11. *Gentiana* Extract[4] | 0.5 |
| 12. Ethanol | 5.0 |
| 13. 1,3-Buthylene glycol | 2.0 |
| 14. Antiseptics | q.s. |
| 15. Fragrance | q.s. |
| 16. Purified water | balance |

[1] Polyether-modified silicone; KF6019 from Shin-Etsu Co., Ltd.
[2] Zinc oxide treated with silicic anhydride: slica with a particle size ranging from 0.01 to 10 μm, containing 50% of zinc oxide; SUNSPHERE SZ-5 from Asahi Glass Company.
[3] *Scuttellaria* Root Extract; extracted with a 50% aqueous 1,3-butylene glycol solution.
[4] *Gentiana* Extract: extracted with a 20% aqueous ethanol solution.

Preparation Procedures
A: Components 6 to 9 were mixed and the resulting mixture was dispersed homogeneously.
B: Components 1 to 5 were mixed and A was added.
C: Components 10 to 14 and 16 were mixed, to which the mixture obtained in B was added and emulsified.
D: The mixture obtained in C was cooled and component 15 was added to obtain cream.

The water-in-oil cream obtained had fine texture and was stable with time. It spread well on the skin and gave non-greasy and refreshing feel to the skin.

Example 20

Eyeliner

| Component | Weight % |
|---|---|
| 1. Decamethylpentasiloxane | 39.0 |
| 2. Polyether-modified silicone[1] | 3.0 |
| 3. Network silicone resin[2] | 15.0 |
| 4. Montmorillonite modified with dioctadecyldimethylammonium salt | 3.0 |
| 5. Iron oxide black treated with the organopolysiloxane of Example 4 | 10.0 |
| 6. 1.3-Butylene glycol | 5.0 |
| 7. Sodium dehydroacetate | q.s. |
| 8. Antiseptics | q.s. |
| 9. Purified water | balance |

[1] Polyether-modified silicone; KF6017 from Shin-Etsu Co., Ltd.
[2] Network silicone resin; KF-7312J from Shin-Etsu Co., Ltd.

Preparation Procedures
A: Components 1 to 4 were mixed and component 5 was added. The resulting mixture was dispersed homogeneously.
B: Components 6 to 9 were mixed.
C: The mixture obtained in B was added dropwise to the mixture obtained in A and emulsified.

The eyeliner obtained was not powdery and stable with time. It spread lightly and gave moisturized and refreshing feel. Applied eyeliner was water and sweat resistant and durable.

Example 21

Foundation

| Component | Weight % |
|---|---|
| 1. Decamethylcyclopentasiloxane | 45.0 |
| 2. Dimethylpolysiloxane (6 mm$^2$/sec at 25° C.) | 5.0 |
| 3. Polyether-modified silicone[1] | 2.0 |
| 4. Montmorillonite modified with Octadecyldimethylbenzylammonium salt | 4.0 |
| 5. Titanium dioxide treated with organopolysiloxane of Example 1 | 10.0 |
| 6. Talc treated with organopolysiloxane of Example 1 | 6.0 |
| 7. Mica treated with organopolysiloxane of Example 1 | 6.0 |
| 8. Iron oxide red treated with organopolysiloxane of Example 1 | 1.6 |
| 9. Iron oxide yellow treated with organopolysiloxane of Example 1 | 0.7 |
| 10. Iron oxide black treated with organopolysiloxane of Example 1 | 0.2 |

-continued

| Component | Weight % |
|---|---|
| 11. Dipropylene glycol | 5.0 |
| 12. Methyl paraoxybenzoate | 0.3 |
| 13. 2-amino-2-methyl-1,3-propanediol | 0.2 |
| 14. Hydrochloric acid | 0.1 |
| 15. Fragrance | q.s. |
| 16. Purified water | balance |

[1]Polyether-modified silicone; KF-6019 from Shin-Etsu Chemical Co., Ltd.

Preparation Procedures

A: Components 1 to 4 were mixed while heating and components 5 to lower added. The resulting mixture was made homogeneous.

B: Components 11 to 14 and 16 were dissolved by heating while the pH of the aqueous phase was kept at 9.0.

C: While stirring, the mixture obtained in B was added dropwise to the mixture obtained in A and emulsifies. After cooling the emulsion, the component 15 was added to obtain foundation.

The foundation obtained had fine texture and was stable with time. It spread lightly on the skin and gave refreshing feel to the skin.

Example 22

Eye Shadow

| Component | Weight % |
|---|---|
| 1. Decamethylcyclopentasiloxane | 15.0 |
| 2. Dimethylpolysiloxane (6 mm$^2$/sec at 25° C.) | 10.0 |
| 3. Branched polyether-modified silicone[1] | 2.0 |
| 4. PEG (10) lauryl ether | 0.5 |
| 5. Chromium oxide treated with organopolysiloxane of Example 2 | 6.2 |
| 6. Ultramarine blue treated with organopolysiloxane of Example 2 | 4.0 |
| 7. Mica coated with titanium treated with organopolysiloxane of Example 2 | 6.0 |
| 8. Sodium chloride | 2.0 |
| 9. Propylene glycol | 8.0 |
| 10. Antiseptics | q.s. |
| 11. Fragrance | q.s. |
| 12. Purified water | balance |

[1]Branched polyether-modified silicone; KF6028 from Shin-Etsu Chemical Co., Ltd.

Preparation Procedures

A: Components 1 to 4 were mixed, to which component 5 to 7 were added and dispersed homogenously.

B: Components 8 to 10 and 12 were dissolved.

C: While stirring, the solution obtained in B was added gradually to the dispersion obtained in A and emulsified, to which component 11 was added.

The eye shadow obtained was not powdery and stable with time. It spread lightly and gave moisturized and refreshing feel to the skin. Applied eyeliner was water and sweat resistant and durable.

Example 23

Lipstick

| Component | Weight % |
|---|---|
| 1. Candelilla wax | 8.0 |
| 2. Polyethylene wax | 8.0 |
| 3. Long-chain alkyl group having acrylic silicone resin[1] | 12.0 |
| 4. Methylphenylpolysiloxane[2] | 3.0 |
| 5. Isotridecyl isononanate | 20.0 |
| 6. Glyceryl isostearate | 16.0 |
| 7. Polyglyceryl triisostearate | 28.5 |
| 8. Red No. 202 treated with organopolysiloxane of Example 4 | 0.8 |
| 9. Iron oxide red treated with organopolysiloxane of Example 4 | 1.5 |
| 10. Iron oxide yellow treated with organopolysiloxane of Example 4 | 1.0 |
| 11. Iron oxide black treated with organopolysiloxane from Preparation Example 4 | 0.2 |
| 12. Titanium dioxide treated with organopolysiloxane of Example 4 | 1.0 |
| 13. Antiseptics | q.s. |
| 14. Fragrance | q.s. |

[1]Long-chain alkyl group containing acrylic silicone resin; KP-561P from Shin-Etsu Chemical Co., Ltd.
[2]Methylphenylpolysiloxane; KF-54 from Shin-Etsu Chemical Co., Ltd.

Preparation Procedures

A: Components 1 to 6 were mixed and part of component 7 was mixed and dissolved.

B: Components 8 to 14 and the rest of the component 7 were mixed homogeneously and the resulting mixture was added to the solution obtained in A, which was poured into a mold.

The lipstick obtained was not powdery and stable with time. It spread lightly and gave moisturized feel to the skin. Applied eyeliner was water and sweat resistant and durable.

Example 24

Lipstick

A lipstick was prepared in the same manner as in Example 23 except the organopolysiloxane of Example 5 was used in place of the organopolysiloxane of Example 4.

The lipstick obtained was not powdery and stable with time. It spread lightly and gave moisturized feel to the skin. Applied eyeliner was water and sweat resistant and durable.

Example 25

Eyeliner

| Component | Weight % |
|---|---|
| 1. Decamethylcyclopentasiloxane | 6.0 |
| 2. Dimethylpolysiloxane (6 mm$^2$/sec at 25° C.) | 5.0 |
| 3. *Jojoba* oil | 2.0 |

-continued

| Component | Weight % |
|---|---|
| 4. Polyether-modified silicone[1] | 1.0 |
| 5. Alkyl/polyether co-modified silicone[2] | 1.0 |
| 6. Acrylic silicone resin[3] | 15.0 |
| 7. Iron oxide black treated with organopolysiloxane of xample 3 | 20.0 |
| 8. Ethanol | 5.0 |
| 9. Antiseptics | q.s. |
| 10. Purified water | q.s. |

[1]Polyether-modified silicone; KF6017 from Shin-Etsu Chemical Co., Ltd.
[2]Alkyl/polyether co-modified silicone; KF6026 from Shin-Etsu Chemical Co., Ltd.
[3]Acrylic silicone resin; KP545 from Shin-Etsu Chemical Co. Ltd Preparation Procedures A: Components 1 to 6 were mixed, to which component 7 was added.

B: Components 8 to 10 were mixed.

C: While stirring, the mixture obtained in B was added gradually to the mixture obtained in A and emulsified.

The eyeliner obtained was not powdery and stable with time. It spread lightly and gave moisturized feel to the skin. Applied eyeliner was water and sweat resistant and durable.

Example 26

Liquid Emulsified Foundation

| Component | Weight % |
|---|---|
| 1. Dimethylpolysiloxane (6 mm$^2$/sec at 25° C.) | 4.5 |
| 2. Decamethylcyclopentasiloxane | 15.0 |
| 3. Squalane | 4.0 |
| 4. Neopentylglycol dioctanoate | 3.0 |
| 5. Myristic acid isostearic acid diglyceride | 2.0 |
| 6. α-Monoisostearyl glyceryl ether | 1.0 |
| 7. Polyether-modified silicone[1] | 1.0 |
| 8. Alkyl/polyether co-modified silicone[2] | 0.5 |
| 9. Aluminum distearate | 0.2 |
| 10. Titanium dioxide treated with organopolysiloxane of Example 2 | 5.0 |
| 11. Sericite treated with organopolysiloxane of Example 2 | 2.0 |
| 12. Talc treated with organopolysiloxane of Example 2 | 3.0 |
| 13. Iron oxide red treated with organopolysiloxane of Example 2 | 0.4 |
| 14. Iron oxide yellow treated with organopolysiloxane of Example 2 | 0.7 |
| 15. Iron oxide black treated with organopolysiloxane of Example 2 | 0.1 |
| 16. Magnesium sulfate | 0.7 |
| 17. Glycerin | 3.0 |
| 18. Antiseptics | q.s. |
| 19. Fragrance | q.s. |
| 20. Purified water | balance |

[1]Polyehter-modifeid silicone; KF6019 from Shin-Etsu Chemical Co., Ltd.
[2]Alkyl/polyether co-modified silicone; KF6026 from Shin-Etsu Chemical Co., Ltd.

Preparation Procedures

A: Components 1 to 9 were mixed while heating, to which component 10 to 15 were added and mixed.

B: Components 16 to 18 and component 20 were dissolved while heating.

C: While stirring, the solution obtained in B was added gradually to the mixture obtained in A and emulsified, The Liquid emulsified foundation obtained had a low viscosity and fine texture. It was stable with time. It spread lightly on the skin and moisturized and refreshing feel to the skin. Applied foundation was sweat resistant and durable.

Example 27

Liquid Foundation

| Component | Weight % |
|---|---|
| 1. Decamethylcyclopentasiloxane | 16.0 |
| 2. Dimethylpolysiloxane (6 mm$^2$/sec at 25° C.) | 8.0 |
| 3. Octyl paramethoxycinnamate | 3.0 |
| 4. 12-Hydroxystearic acid | 1.0 |
| 5. Fluorine-modified silicone[1] | 15.0 |
| 6. Fluorinated alkyl/polyether co-modified silicone[2] | 5.0 |
| 7. Powder of spherical polymethylsilsesquioxane[3] | 3.0 |
| 8. Fine powder of titanium dioxide treated with organopolysiloxane of Example 3 | 8.0 |
| 9. Mica titanium dioxide treated with organopolysiloxane of Example 3 | 1.0 |
| 10. Titanium dioxide treated with organopolysiloxane of Example 3 | 5.0 |
| 11. Iron oxide red treated with organopolysiloxane of Example 3 | 0.9 |
| 12. Iron oxide yellow treated with organopolysiloxane of Example 3 | 2.0 |
| 13. Iron oxide black treated with organopolysiloxane of Example 3 | 1.0 |
| 14. Ethanol | 15.0 |
| 15. Glycerin | 3.0 |
| 16. Magnesium sulfate | 1.0 |
| 17. Antiseptics | q.s. |
| 18. Fragrance | q.s. |
| 19. Purified water | balance |

[1]Fluorine-modified silicone; FL-50 from Shin-Etsu Chemical Co., Ltd.
[2]Flouorinated alkyl/polyether-comodified silicone; FPD-4694 from Shin-Etsu Chemical Co., Ltd.
[3]Powder of spherical polymethylsilsesquioxane; KMP 590 50 from Shin-Etsu Chemical Co., Ltd.

Preparation Procedures

A: Components 7 to 13 were mixed.

B: Components 1 to 6 were mixed while heating to 70° C., to which the mixture obtained in A was added and dispersed.

C: The components 14 to 17 and components 19 were mixed and heated to 40° C.

D: The mixture obtained in C was added to the dispersion obtained in B and emulsified. Then, the emulsion was cooled, to which component 18 was added.

The liquid foundation obtained was stable with time. It spread lightly on the skin and gave refreshing feel to the skin. Applied foundation was sweat resistant and durable.

Example 28

Eyeliner

| Component | Weight % |
|---|---|
| 1. Decamethylcyclopentasiloxane | 22.0 |
| 2. Dimethylpolysiloxane (6 mm$^2$/sec at 25° C.) | 5.0 |
| 3. Iron oxide black treated with organopolysiloxane of Example 1 | 20.0 |
| 4. Network silicone resin[1] | 10.0 |
| 5. Vitamin E acetate | 0.2 |
| 6. *Jojoba* oil | 2.0 |
| 7. Bentonite | 3.0 |
| 8. Polyether-modified silicone[2] | 2.0 |

-continued

| Component | Weight % |
| --- | --- |
| 9. Ethanol | 3.0 |
| 10. 1,3-Butylene glycol | 5.0 |
| 11. Antiseptics | q.s. |
| 12. Purified water | balance |

[1] Organosilicone resin; KF-7312J from Shin-Etsu Chemical Co., Ltd.
[2] Polyether-modified silicone; KF6017 from Shin-Etsu Chemical Co., Ltd.

Preparation Procedures

A: Components 1, 2, and 4 to 8 were mixed, to which component 3 was added and dispersed.

B: Components 9 to 11 and 13 were mixed.

C: The mixture obtained in B was added gradually to the mixture obtained in A and emulsified, and then cooled.

The eyeliner obtained was stable with time. It spread lightly and gave refreshing feel. Applied eyeliner was water and sweat resistant and durable.

Example 29

Foundation

| Component | Weight % |
| --- | --- |
| 1. Decamethylcyclopentasiloxane | 27.0 |
| 2. Methylphenylpolysiloxane | 3.0 |
| 3. Glyceryl trioctanoate | 10.0 |
| 4. Branched polyglycerin-modified silicone[1] | 1.0 |
| 5. Polyglyceryl monoisostearate | 3.0 |
| 6. Mixture of hydrophobized powders[2] | 18.0 |
| 7. Iron oxide red | 1.2 |
| 8. Iron oxide yellow | 2.6 |
| 9. Iron oxide black | 0.2 |
| 10. 1,3-Butylene glycol | 7.0 |
| 11. Sodium chloride | 0.5 |
| 12. Antiseptics | q.s. |
| 13. Fragrance | q.s. |
| 14. Purified water | balance |

[1] Branched polyglycerin-modified silicone; KF6104 from Shin-Etsu Chemical Co., Ltd.
[2] Mixture of hydrophobized powders:

| | weight % |
| --- | --- |
| a. Fine powder of titanium dioxide | 8.0 |
| b. Fine powder of zinc oxide | 4.0 |
| c. Talc | 3.0 |
| d. Mica | 3.0 |

Preparation Procedures

A: Components a to d were mixed. To the resulting powder mixture, 1 wt. %, based on the weight of the mixture, of organopolysiloxane of Example 1 was added and heated to treat the powder.

B. Components 1 to 5 were mixed while heating, to which components 6 to 9 were added and dispersed.

C. Components 10 to 12 and 14 were mixed, which then was added to the dispersion obtained in B and emulsified.

D: The emulsion obtained in C was cooled.

The foundation obtained was stable with time. It spread lightly on the skin and gave glossy and durable finish.

Example 30

Hair Spray for Brushing

| Component | Weight % |
| --- | --- |
| 1. Isopropyl myristate | 1.0 |
| 2. Stearyltrimethylammonium chloride | 0.1 |
| 3. Zinc oxide treated with organopolysiloxane of Example 1 | 3.0 |
| 4. Ethanol | 25.0 |
| 5. Fragrance | q.s. |
| 6. Blowing agent | balance |

Preparation Procedures

A: Components 1 to 5 were mixed.

B: The mixture obtained in A was packed into an aerosol can and then component 6 was packed to obtain brushing agent.

In the brushing spray thus obtained, powder was well dispersed. It gave a shiny and smooth, and easy to comb hair.

Example 31

Rinse

| Component | Weight % |
| --- | --- |
| 1. Ethylene glycol distearate | 3.0 |
| 2. Cetanol | 2.0 |
| 3. Propylene glycol monostearate | 3.0 |
| 4. Dimethylpolysiloxane (100 mm$^2$/sec at 25° C.) | 3.0 |
| 5. Glycerin monostearate | 4.0 |
| 6. Polyoxyethylene (3) stearate | 4.0 |
| 7. Acetyltrimethylammonium chloride | 5.0 |
| 8. Polyoxyethylene (20) cetyl ether | 2.0 |
| 9. Zinc oxide treated with organopolysiloxane of Example 1 | 2.0 |
| 10. 1,3-Butylene glycol | 5.0 |
| 11. Antiseptics | q.s. |
| 12. Fragrance | q.s. |
| 13. Purified water | balance |

Preparation Procedures

A: Components 1 to 9 were mixed.

B. Components 10, 11 and 13 were mixed while heating.

C: The mixture obtained in B was mixed with the mixture obtained in A and then cooled, to which component 12 was added.

The rinse obtained was stable with time and gave gloss and easiness to comb to the hair.

Example 32

No Rinse Shampoo

| Component | Weight % |
| --- | --- |
| 1. Lauric acid amide propyldimethylaminoacetic acid betaine (30%) | 15.0 |
| 2. Sodium polyoxyethylene (3) lauryl ether sulfate (27%) | 4.0 |
| 3. Polyoxyethylene (150) distearate | 0.5 |
| 4. Cationized cellulose (4%) | 0.5 |
| 5. Glycerin | 3.0 |
| 6. Dimethylpolysiloxane (1,000,000 mm$^2$/sec at 25° C.) | 1.0 |
| 7. Dimethylpolysiloxane (100 mm$^2$/sec at 25° C.) | 3.0 |
| 8. Mica treated with organopolysiloxane of Example 1 | 2.0 |
| 9. Antiseptics | q.s. |
| 10. Fragrance | q.s. |
| 11. Purified water | balance |

Preparation Procedures

A: Components 1 to 5, 9 and 11 were mixed while heating.

B. Components 6 to 8 were mixed and dispersed.

C: The dispersion obtained in B was added to the mixture obtained in A and then cooled, to which component 10 was added.

The no-rinse shampoo obtained was stable with time and gave gloss and easiness to comb to the hair.

Example 33

Treatment

| Component | Weight % |
| --- | --- |
| 1. Ethylene glycol distearate | 1.0 |
| 2. Liquid paraffins | 10.0 |
| 3. Squalane | 5.0 |
| 4. Stearyl alcohol | 1.5 |
| 5. Dimethylpolysiloxane (10 mm$^2$/sec at 25° C.) | 3.0 |
| 6. Stearic acid | 6.0 |
| 7. Polyoxyethylene (3) stearyl alcohol | 4.5 |
| 8. Polyoxyethylene (150) cetyl alcohol | 2.0 |
| 9. Sericite treated with organopolysiloxane of Example 4 | 1.5 |
| 10. 1,3-Butylene glycol | 6.0 |
| 11. Antiseptics | q.s. |
| 12. Fragrance | q.s. |
| 13. Purified water | balance |

Preparation Procedures

A: Components 1 to 9 were mixed while heating.

B. Components 10, 11, and 13 were mixed and dispersed.

C: The dispersion obtained in B was added to the mixture obtained in A and then cooled, to which Component 12 was added.

The treatment obtained was stable with time and non-sticky. It gave gloss and easiness to comb.

Example 34

Water-In-Oil Type Antiperspirant

| Component | Weight % |
| --- | --- |
| 1. Crosslinked polyether-modified silicone[1] | 7.0 |
| 2. Decamethylcyclopentasiloxane | 10.0 |
| 3. Glyceryl trioctanoate | 7.0 |
| 4. Dipropylene glycol | 5.0 |
| 5. Sodium citrate | 0.2 |
| 6. Aluminum zirconium tetrachlorohydrate | 18.0 |
| 7. Zinc oxide treated with organopolysiloxane of Example 2 | 5.0 |
| 8. Composite powder of fluorine-modified hybrid silicone[2] | 2.0 |
| 9. Fragrance | q.s. |
| 10. Purified water | 45.8 |

[1] Crosslinked polyether-modified silicone; KSG-210 from Shin-Etsu Chemical Co., Ltd.

[2] Composite powder of fluorine-modified hybrid silicone; KSP-200 from Shin-Etsu Chemical Co., Ltd.

Preparation Procedures

A: Components 1 to 3 were mixed.

B. Components 4 to 10 were mixed.

C: The mixture obtained in B was added to the mixture obtained in A and emulsified.

The Water-in-oil type antiperspirant thus obtained was stable with time. It spread lightly and gave refreshing feel to the skin.

Example 35

Antiperspirant of Roll-On-Type

| Component | Weight % |
| --- | --- |
| 1. Crosslinked polyether-modified silicone[1] | 20.0 |
| 2. Dimethylpolysiloxane (6 mm$^2$/sec at 25° C.) | 10.0 |
| 3. Crosslinked dimethylpolysiloxane[2] | 15.0 |
| 4. Decamethylcyclopentasiloxane | 30.0 |
| 5. Aluminum/zirconium tetrachlorohydrate | 20.0 |
| 6. Zinc oxide treated with organopolysiloxane of Example 1 | 5.0 |
| 7. Fragrance | q.s. |

[1] Crosslinked polyether-modified silicone; KSG-210 from Shin-Etsu Chemical Co., Ltd.

[2] Crosslinked dimethylpolysiloxane; KSG-15 from Shin-Etsu Chemical Co., Ltd.

Preparation Procedures

A: Components 1 to 4 were mixed.

B. To the mixture obtained in A, components 5 to 7 were added and dispersed.

The roll-on-type antiperspirant thus obtained was stable with time. It spread lightly and gave refreshing feel to the skin.

Example 36

Suncut Milky Lotion

| Component | Weight % |
|---|---|
| 1. Decamethylcyclopentasiloxane | 20.0 |
| 2. Methylphenylpolysiloxane | 3.0 |
| 3. Sorbitan monoisostearate | 1.0 |
| 4. Polyether-modified silicone[1] | 0.5 |
| 5. Trimethylsiloxy cinnamate[2] | 1.0 |
| 6. Octyl paramethoxy cinnamate | 4.0 |
| 7. Titanium dioxide treated with organopolysiloxane of Example 1 | 8.0 |
| 8. Sorbitol | 2.0 |
| 9. Sodium chloride | 2.0 |
| 10. Antiseptics | q.s. |
| 11. Fragrance | q.s. |
| 12. Purified water | balance |

[1]Polyether-modified silicone; KF-6015 from Shin-Etsu Chemical Co., Ltd.
[2]Trimethylsiloxy cinnamate; X-21-5250 from Shin-Etsu Chemical Co., Ltd.

Preparation Procedures
A: Components 1 to 6 were mixed while heating and component 7 was dispersed.
B. Components 8 to 10, and 12 were mixed while heating.
C: While stirring, the mixture obtained in B was added gradually to the dispersion obtained in A and emulsified. The emulsion was cooled, to which component 11 was added.

The suncut milky lotion thus obtained was stable with time and has fine texture. It spread lightly on the skin. It was not greasy and the applied lotion was durable to keep UV protection effect for a prolonged period of time.

Example 37

Suncut Cream

| Components | Weight % |
|---|---|
| 1. Decamethylcyclopentasiloxane | 17.5 |
| 2. Acrylic silicone resin[1] | 12.0 |
| 3. Glyceryl trioctanoate | 5.0 |
| 4. Octyl paramethoxy cinnamate | 6.0 |
| 5. Crosslinked polyether-modified silicone[2] | 5.0 |
| 6. Alkyl/polyether co-modified silicone[3] | 1.0 |
| 7. Zinc oxide treated with organopolysiloxane of Example 2 | 20.0 |
| 8. Sodium chloride | 0.5 |
| 9. 1,3-Butylene glycol | 2.0 |
| 10. Antiseptics | q.s. |
| 11. Fragrance | q.s. |
| 12. Purified water | balance |

[1]Acrylic silicone resin; KP545 from Shin-Etsu Chemical Co., Ltd.
[2]Crosslinked polyether-modified siicone; KSG210 from Shin-Etsu Chemical Co., Ltd.
[3]Alkyl/polyether co-modified silicone; KF6026 from Shin-Etsu Chemical Co., Ltd.

Preparation Procedures
A: Component 2 was added to a part of component 1 and mixed, to which component 7 was added and dispersed with a bead mill.
B: The rest of the component 1 and components 3 to 6 were mixed.
C: Components 8 to 10 and 12 were mixed and dissolves.
D: The solution obtained in C was added to the mixture obtained in B and emulsified, to which the emulsion obtained in A and component 11 were added.

The suncut cream thus obtained was stable with time. It was not greasy and spread lightly on the skin. The applied cream was durable to keep UV protection effect for a prolonged period of time.

The invention claimed is:

1. A powder treated with a powder treating agent selected from the group consisting of:

$[(CH_3)_3SiO_{1/2}]_3[(CH_3)_2SiO]_{10}[(CH_3)HSiO]_5[CH_3SiO_{3/2}]_1;$ $[(CH_3)_3SiO_{1/2}]_3[(CH_3)_2SiO]_{30}[(CH_3)HSiO]_{10}[C_8H_{17}SiO_{3/2}]_2;$ $[(CH_3)_3SiO_{1/2}]_3[(CH_3)(CF_3C_2H_4)SiO]_3[(CH_3)HSiO]_{30}[C_8H_{17}SiO_{3/2}]_2;$ $[(CH_3)_3SiO_{1/2}]_4[(CH_3)_2SiO]_{20}[(CH_3)HSiO]_{10}[SiO_2];$ and $[(CH_3)_3SiO_{1/2}]_6[(CH_3)_2SiO]_{30}[(CH_3)HSiO]_{10}[C_8H_{17}SiO_{3/2}]_2[SiO_2].$ 2. The powder according to claim 1, wherein the powder is selected from the group consisting of zinc oxide, titanium oxide, mica, sericite, talc, and kaolin.

3. A cosmetic comprising the powder according to claim 1.

4. The cosmetic according to claim 3, wherein the cosmetic further comprises an unctuous agent (B).

5. The cosmetic according to claim 4, wherein the unctuous agent (B) is a linear or cyclic silicone oil represented by the following formula:

$$R^3_k SiO_{(4-k)/2}$$

wherein $R^3$ is selected from the group consisting of a hydrogen atom, and alkyl, aryl, aralkyl, and fluorinated alkyl groups each having 1 to 30 carbon atoms and k is the number of from 0 to 2.5.

6. The cosmetic according to claim 3, wherein the cosmetic further comprises water (C).

7. The cosmetic according to claim 3, wherein the cosmetic further comprises a compound (D) having an alcoholic hydroxyl group.

8. The cosmetic according to claim 7, wherein the compound (D) is at least one selected from the group consisting of water-soluble monohydric alcohols and water-soluble polyhydric alcohols.

9. The cosmetic according to claim 3, wherein the cosmetic further comprises a water-soluble or water-swelling polymer (E).

10. The cosmetic according to claim 3, wherein, the cosmetic further comprises powder (F) other than the powder according to claim 1.

11. The cosmetic according to claim 10, wherein at least a part of the powder (F) is crosslinked dimethyl silicone powder, polymethylsilsesquioxane powder, hydrophobicized silica powder, or spherical silicone rubber powder whose surface is coated with polymethylsilsesquioxane particles.

12. The cosmetic according to claim 3, wherein the cosmetic further comprises a surfactant (G).

13. The cosmetic according to claim 12, wherein the surfactant (G) is a linear or branched silicone having a polyoxyalkylene chain moiety.

14. The cosmetic according to claim 12, wherein the surfactant (G) has an HLB of from 2 to 8.

15. The cosmetic according to claim 3, wherein the cosmetic further comprises at least one silicone resin (H) selected from the group consisting of acrylic silicone resins and silicones having a network structure expressed as MQ, MDQ, MT, MDT, or MDTQ.

16. The cosmetic according to claim 15, wherein the silicone resin (H) has at least a moiety selected from the group consisting of pyrrolidone residue, long-chain alkyl group, polyoxyalkylene group, fluoroalkyl group, amino group and carboxyl group.

17. The cosmetic according to claim 3, wherein the cosmetic is a skin care cosmetic, a makeup cosmetic, a hair-care cosmetic, an antiperspirant cosmetic, or a UV ray protective cosmetic.

18. The cosmetic according to claim 3, wherein the cosmetic is in the form of liquid, emulsion, cream, solid, paste, gel, powder, pressed powder, mousse, spray, stick, or pencil.

* * * * *